United States Patent [19]

Levine et al.

[11] 4,165,343
[45] Aug. 21, 1979

[54] DEHYDRATION OF TERTIARY BUTYL ALCOHOL

[75] Inventors: Ralph Levine, Freehold; Jerome R. Olechowski, Lawrenceville, both of N.J.

[73] Assignee: Cities Service Conmpany, Tulsa, Okla.

[21] Appl. No.: 929,075

[22] Filed: Jul. 28, 1978

[51] Int. Cl.$^2$ .............................................. C07C 5/22
[52] U.S. Cl. ................................................... 585/638
[58] Field of Search ........................................ 260/682

[56] References Cited

U.S. PATENT DOCUMENTS

| 3,256,250 | 6/1966 | Frilette | 260/682 |
|---|---|---|---|
| 3,510,538 | 5/1970 | Rosenthal | 260/682 |
| 4,065,512 | 12/1977 | Cares | 260/682 |

*Primary Examiner*—C. Davis
*Attorney, Agent, or Firm*—Richard D. Stone; Patricia J. Hogan

[57] ABSTRACT

Tertiary butyl alcohol is dehydrated in the presence of para-toluene sulfonic acid catalyst and xylene which forms an azeotrope with the water of hydration. Isobutylene and water, formed by the dehydration reaction, along with xylene, are removed as a vapor fraction. Xylene serves a dual purpose, acting as a solvent for paratoluene sulfonic acid so that this catalyst can contact the tertiary butyl alcohol feed, and also acting as an azeotrope forming agent to remove water as it is formed and to promote the dehydration reaction.

10 Claims, No Drawings

DEHYDRATION OF TERTIARY BUTYL ALCOHOL

BACKGROUND OF THE INVENTION

Field of the Invention

This invention relates to a method for the continuous dehydration of tertiary butyl alcohol, TBA, using an acid catalyst. Water formed in the dehydration reaction is continuously removed from the reaction zone as an azeotrope with xylene.

The dehydration of tertiary butyl alcohol to form isobutylene is well known.

The reaction is a relatively simple one, high temperature alone will convert tertiary butyl alcohol to isobutylene though it is usually preferred to use a catalyst.

Catalysts which have been used in the past have ranged from none, to alumina, to sulfuric acid and resin sulfonic acids.

U.S. Pat. No. 3,510,538 (U.S. Class 260–682), the teachings of which are incorporated by reference, discloses a continuous process for dehydration of tertiary butyl alcohol which uses as an acid acting catalyst a cation exchange resin, preferably a sulfonic acid type cation exchange resin.

This reference also discloses the use of benzene in the dehydration zone. The benzene forms an azeotrope with water produced by dehydration of tertiary butyl alcohol, TBA. The benzene-water azeotrope and produced isobutylene are removed as a vapor fraction from the dehydration zone. The vapors are cooled sufficiently to condense benzene and water, but not enough to condense isobutylene. A water phase is withdrawn from the process, benzene is recycled to the dehydration zone, and isobutylene product recovered as a vapor fraction.

The benzene removes water by azeotrope formation as the water is formed in the dehydration zone. This makes the dehydration zone essentially anhydrous, which promotes very high dehydration rates.

The patentee taught that reaction temperatures of 68° to 100° C. could be used, but that temperatures above 100° C. should be avoided because isobutylene begins to dimerize appreciably at the higher temperatures. The patentee taught that although other hydrocarbons form azeotropes with water, benzene was the only compound suitable for use.

The process described is reasonably satisfactory, but not very efficient in handling TBA feed streams which contain a significant amount of water. The use of cation exchange resins as catalyst also is not desirable in that three phases are necessarily present in the reaction zone, solid, liquid, and gaseous. Presence of solid catalyst necessarily introduces problems of catalyst containment, and catalyst attrition. These problems are not impossible to overcome but do increase the complexity and cost of a dehydration reaction zone.

Finally, it would be very desirable if somewhat higher rates of reaction could be obtained. The system described in U.S. Pat. No. 3,510,538 gives relatively low conversion rates of tertiary butyl alcohol because of problems in ensuring that the liquid reactants adequately contact the particulate catalyst, and also because of the relatively low reaction zone temperatures which must be used to minimize dimerization.

Use of aryl sulfonic acids for dehydration is well known. Use of PTSA for hydration of isobutylene is also known.

SUMMARY OF THE INVENTION

We have discovered a unique catalyst system comprising an sulfonic acid and xylene which substantially overcomes the problems encountered in prior art dehydration processes.

We have discovered that use of a liquid catalyst, dissolved in a hydrocarbon solvent, gives excellent dehydration, without the problems associated with particulate catalyst.

We have discovered a unique azeotrope forming agent which permits operation at higher temperatures, without excessive dimerization.

Accordingly, the present invention provides a method of dehydrating tertiary butyl alcohol to isobutylene which comprises contacting in a reaction zone the tertiary butyl alcohol in the presence of a xylene with a sulfonic acid catalyst at a temperature of 70° to 200° C.

DETAILED DESCRIPTION OF INVENTION

The preferred acid acting catalyst is para-toluenesulfonic acid, PTSA, or ortho-toluene sulfonic acid, OTSA, or mixture thereof.

The amount of catalyst used is not critical. It is preferred to operate with a solvent saturated with the preferred catalyst. PTSA is slightly soluble in xylene at temperatures encountered in the reaction zones. The solubility of PTSA in xylene increases as the concentration of TBA in xylene increases. In practice, adding enough PTSA to maintain a small amount of liquid PTSA in the bottom of the reaction zone gives good results.

Other aryl sulfonic acids may be used, but not necessarily with equivalent results. It may be possible to use a sulfonic acid derived from a long chain normal paraffin.

It should be possible to use other sulfonic acid catalysts, such as resin sulfonic acid catalysts, but these are not preferred because of the difficulties caused by a solid phase and because less favorable production rates and/or product purity may be obtained.

The catalyst should be able to withstand temperatures encountered in the reaction zone. Some resin sulfonic acid catalysts may not be stable at temperatures over 100° C.

The feed to the process is tertiary butyl alcohol, TBA, which usually will contain significant amounts of water depending upon the source of the feed. Water can be tolerated in the feed because it is removed from the reaction zone as an azeotrope. Water in the feed is not desirable becauses it increases the amount of water and xylene which must be removed from the reaction zone.

The azeotrope forming agent is a xylene, preferably paraxylene. Mixed xylenes are inexpensive and readily available in the market place. Paraxylene is somewhat more expensive, but also readily available because it is a very popular chemical intermediate. Use of a xylene as the azeotrope forming agent is preferred over lighter hydrocarbons because the xylene results in significantly higher operating temperatures in the dehydration zone than can be obtained with a lighter azeotrope forming agent, such as benzene. Use of paraxylene is especially preferred, because paraxylene is relatively immune from butylation. TBA, or perhaps isobutylene, react to some extent with orthoxylene and metaxylene. This is undesirable as it results in wasteful consumption of isobutylene, or its percursor, TBA, changes the character of the azeotrope forming agent, and increases the molecular weight of the azeotrope forming agent causing more energy to be expended in vaporizing and condensing it.

Reaction conditions which may be used in the dehydration reaction zone include those of the prior art, and higher temperatures as well. The lower limit on temperature is around 60° C. The reaction rate is very slow at this temperature, and is not really practical for commercial operation. The upper limit on temperature is believed to be between 150° to 200° C. At temperatures of 150° C. and above some significant dimerization may occur, and in one instance some butadiene formation was noted.

Pressure required in the dehydration zone is that sufficient to maintain the xylene in a liquid hydrocarbon phase. It may be desirable to operate at super atmospheric pressures, 4 to 8 atmospheres, absolute, to facilitate condensation of vapor products from the dehydration reaction zone. Operation at atmospheric pressure is possible, because refrigeration is necessary to condense reactor effluent vapors. Alternatively, low pressure reactor effluent vapors may be compressed.

It is possible to add additional hydrocarbons to the xylene when some modifications of the azeotrope forming agent are needed. Addition of lighter hydrocarbons may be used to lower the reaction zone temperature, while heavier materials may be added to increase the temperature in the reaction zone, while maintaining a constant pressure. Addition of aromatic hydrocarbons heavier or lighter than xylenes should probably be avoided because of the danger of alkylation of these materials. Paraffin hydrocarbons can probably be used to alter the solvent's characteristics without the danger of reacting with the feed. Examples of heavier materials which can be added to the xylene fraction are ethylene glycol diacetate and dimethyl phthalate.

EXAMPLE I

A series of tests were run to determine the effecttiveness of various prior art processes for dehydrating TBA to isobutylene. To provide a reference point, a number of tests were made without a catalyst, but with an azeotrope forming agent.

A dehydration zone, consisting of a stoppered flask with an electrically heated jacket around it, was charged with TBA and mixed xylenes. Vapor from the dehydration zone was cooled causing xylene and water to condense. Liquid xylene was recycled or refluxed to the dehydration flask and the water was separately removed. Essentially, nothing happened.

EXAMPLE II

The experiments of Example I were repeated using an aqueous solution of PTSA, 63 wt % PTSA and the remainder water.

No hydrocarbon azeotropic forming agent was present.

The dehydration rate at 80° C. was about one percent per hour. A repeat of this experiment at 105°–110° C. increased the dehydration rate to about ten percent per hour.

EXAMPLE III

The experiments of Examples I and II were repeated within a flask containing about 10 grams of PTSA, which is really a mixture of 90% PTSA, 10% OTSA, approximately, and about 110 grams of mixed xylenes. Two liquid phases were present with PTSA the lower phase. TBA feed was added dropwise to the flask. The flask was surrounded by an electric heater connected to a powerstat, which could maintain constant power input. TBA addition rate was adjusted to hold a constant temperature within the flask.

The catalyst system within the flask consists of a small liquid phase of PTSA in the bottom of the vessel covered by a very large liquid layer of mixed xylenes. The solubility of PTSA in xylene is around 0.1–0.2 wt %, depending on temperature. A significant amount of TBA can dissolve in the xylene, and probably must dissolve there to contact the catalyst. TBA dissolved in the xylene can increase the solubility of PTSA in the xylene fraction. The precise composition of the catalyst system at any given time has not been determined. The catalyst system may operate with a fairly high concentration of TBA and consequently of PTSA, or the catalyst system may be so effective that only very minor amounts of TBA remain in the xylene solution before the dehydration reaction is completed.

If the reaction rate slows down the amount of TBA in the xylene will increase, causing the amount of PTSA catalyst in the xylene phase to increase, which should help increase the reaction rate.

The following table shows the experimental results obtained when using different types of TBA feed and solvent.

In all cases, the catalyst used was 3 to 10 g PTSA in solvents. Feed was added, dropwise, to a flask containing about 100 to 130 grams of solvent. Adding more than 3 grams of PTSA did not seem to have much effect on reaction rate. It is believed that the solvent was saturated, at conditions experienced in the reaction zone, with 3 wt % PTSA, and adding more catalyst merely increased the size of the pool of PTSA in the bottom of the flask. These were preliminary tests designed to quickly determine the suitability of various solvents.

TABLE I

DEHYDRATION TBA/H$_2$O AND TBA TO ISOBUTYLENE

| TBA/H$_2$O | Solvent | Temp. °C. | Conversion % | % i-C$_4$= In Product | % Dimer In Product |
|---|---|---|---|---|---|
| 80/20 | none | 80–96 | 32.3 | 99.23 | 0.47 |
| 100/0 | xylene | 80–126 | 83.7 | 99.54 | 0.46 |
| 100/0 | xylene | 80–126 | 83.7 | 99.09 | 0.87 |
| 88/12 | xylene | 100–120 | 90.3 | 95.52 | 0.48 |
| 88/12 | xylene, 27 g ethylene glycol diacetate, 75 g PTSA, 11 g | 140–150 | n.a. | 99.75* | — |

TABLE I-continued
DEHYDRATION TBA/H₂O AND TBA TO ISOBUTYLENE

| TBA/H$_2$O | Solvent | Temp. °C. | Conversion % | % i-C$_4$- In Product | % Dimer In Product |
|---|---|---|---|---|---|
| 88/12 | xylene, 66 g dimethyl phthalate, 44 g, PTSA, 3.5 g | 125–144 | 97.0 | 99.38 | 0.20 |

*Vapor phase chromatography indicated 0.25% 1,3-butadiene

All of these experiments were conducted with a mixed xylene fraction. An analysis of the xylenes indicated that a significant amount of butylation had occurred, except for the paraxylene which had survived 20 to 25 uses in the reaction zone without attack. The xylene feed contained 1 LV% toluene, 1 LV% unknowns, and 98 LV% mixed xylenes. An analysis of the xylene after several uses is presented below, in Table II.

TABLE II

| Sulfones | 0.015 wt % |
|---|---|
| 4-t butyl o-xylene | 31 wt % |
| 5-t butyl m-xylene | 5 wt % |
| di-isobutylene | 5 wt % |
| mixed C8 aromatics | remainder |
| butylated p-xylene | none |

Toluene solvent was also tested, as a substitute for mixed xylenes. The boiling point of the toluene increased, indicating some reaction had occurred between the catalyst-TBA—isobutylene—toluene system.

When operating with a TBA feed which contains water, and many TBA feed streams will contain water, it may be desirable to add the TBA feed to the overhead system used to receive dehydration zone vapors. Some significant amount of water in the TBA feed may be removed by phase separation in the overhead receiver, permitting water which was present in the feed to be removed as a separate aqueous phase, with only minimal loss of TBA. The loss of TBA is minimal because most of the TBA will preferentially dissolve in the xylene azeotrope forming agent.

We claim:

1. A process for dehydrating t-butyl alcohol to isobutylene which comprises contacting the t-butyl alcohol with a liquid sulfonic acid catalyst in the presence of a xylene at a temperature of 70°–200° C. in a reaction zone.

2. The process of claim 1 wherein the catalyst is an arylsulfonic acid.

3. The process of claim 2 wherein the arylsulfonic acid is a member of the group consisting of p-toluenesulfonic acid, o-toluenesulfonic acid, and mixtures thereof.

4. The process of claim 1 wherein the xylene is p-xylene.

5. The process of claim 1 wherein the reaction zone also contains a modifier selected from the group consisting of paraffins, ethylene glycol diacetate, and dimethyl phthalate.

6. The process of claim 1 wherein the temperature is 100°–150° C.

7. The process of claim 1 wherein the pressure in the reaction zone is sufficient to maintain the xylene in a liquid phase.

8. The process of claim 1 wherein at least a portion of the water produced is removed from the reaction zone as an azeotrope with xylene.

9. The process of claim 1 wherein t-butyl alcohol is contacted with a liquid sulfonic acid of the group consisting of p-toluenesulfonic acid, o-toluenesulfonic acid, and mixtures thereof in the presence of p-xylene at a temperature of 100°–150° C. and under pressure sufficient to maintain the xylene in a liquid phase, and at least a portion of the water produced is removed from the reaction zone as an azeotrope with xylene.

10. The process of claim 9 wherein the reaction zone also contains a modifier of the group consisting of paraffins, ethylene glycol diacetate, and dimethyl phthalate.

* * * * *